United States Patent [19]
Yoshida et al.

[11] Patent Number: 5,436,372
[45] Date of Patent: Jul. 25, 1995

[54] SOLID STATE DISPLACEMENT ELEMENTS

[75] Inventors: Hiroyuki Yoshida, Aichi; Eturo Yasuda, Okazaki; Yoshiaki Fukushima, Aichi, all of Japan

[73] Assignee: Nippon Soken, Inc., Nishio, Japan

[21] Appl. No.: 865,617

[22] Filed: Apr. 9, 1992

[30] Foreign Application Priority Data

Apr. 9, 1991 [JP] Japan .................................. 3-076445

[51] Int. Cl.$^6$ ............................................ C07C 211/03
[52] U.S. Cl. .................................... 564/291; 564/463; 564/63; 564/32; 564/441; 564/305; 564/502; 568/852; 568/382; 562/574; 562/433; 562/434; 562/512; 546/326
[58] Field of Search ................................ 564/463, 291

[56] References Cited

FOREIGN PATENT DOCUMENTS 58-45107   3/1983   Japan .
62-212205  9/1987   Japan .
63-215775  9/1988   Japan .

OTHER PUBLICATIONS

Ruiz et al. CA95:27922a. 1981.
Aragon de La et al. CA91:63175k. 1979.
Van Assche et al. CA81:111728k. 1974.
Aragon de La et al. CA79:35415x 1973.
Takagi et al. CA70:39338m 1969.
"Intercalation Compounds of clays" (Kato et al.) Nendo Kagaku vol. 26 No. 4, 292–305 (1986).

*Primary Examiner*—Jane Fan
*Attorney, Agent, or Firm*—Cushman, Darby & Cushman

[57] ABSTRACT

The invention is intended to provide novel solid state displacement elements that have an extent of displacement. The solid state displacement element has an intercalation compound in which a polar compound (B) is mixed with an inorganic layered compound (A), and produces a strain when a voltage is applied.

13 Claims, 3 Drawing Sheets

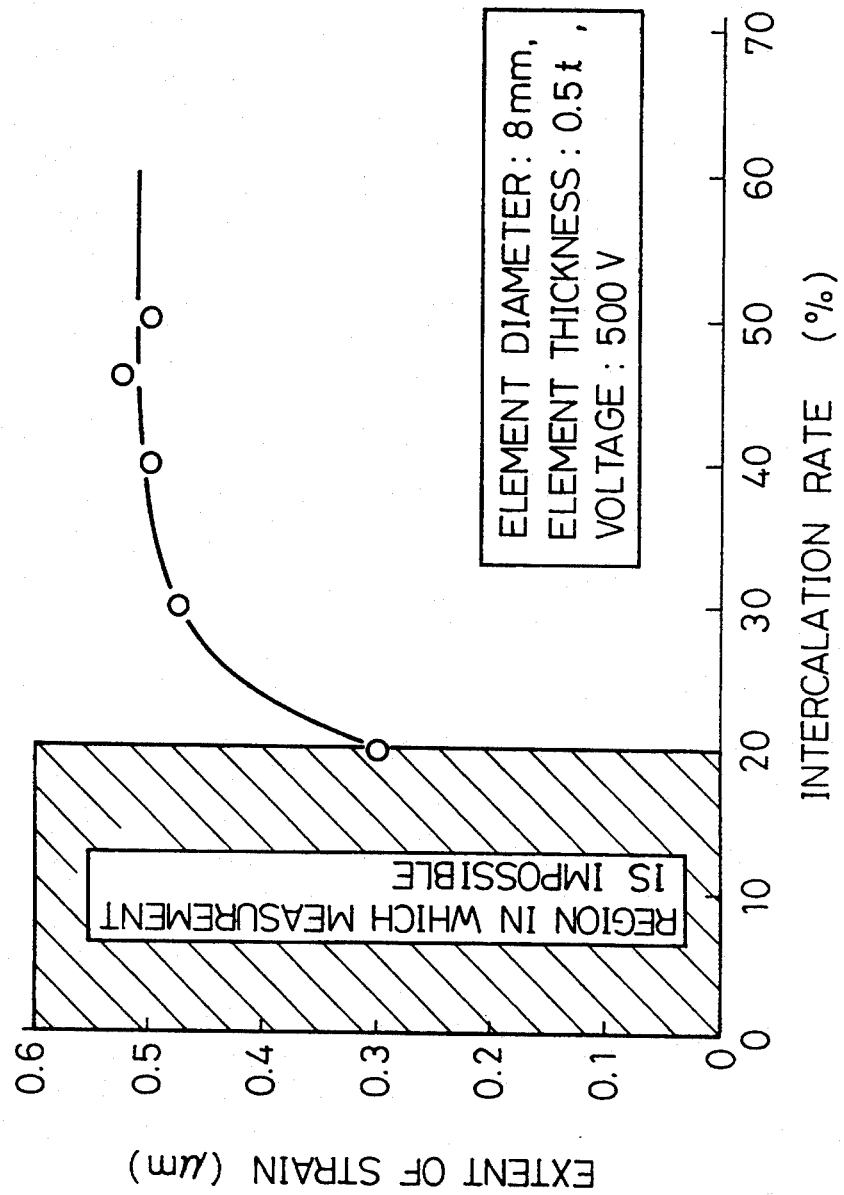

SOLID STATE DISPLACEMENT ELEMENTS

BACKGROUND OF THE INVENTION

1. Field of the Invention

This invention concerns solid state displacement elements comprised principally of inorganic layered compounds and in which a strain is produced when a voltage is applied.

2. Description of the Related Art

Electrostrictive type actuators constructed from solid state displacement elements in which a strain is produced when a voltage is applied, for example, for driving damping force control valves for vehicles and fuel injection valves or fuel control valves for the fuel injection devices of internal combustion engines etc.

However, the electrostrictive elements that have been used in the past have generally been formed with ceramics in which lead zirconate titanate (PZT) forms the principal component. These are manufactured using the methods of powder metallurgy. That is to say, raw materials comprising of 61.3 wt. % of PbO, 10.7 wt. % of $TiO_2$ and 21.1 wt. % of $ZrO_2$ as the principal components are weighed out and mixed by wet ball-milling. The mixture is then pre-baked for 3–10 hours at 700°–900° C. and then ball-milled again and dried. A binder such as poly (vinyl alcohol) is then added and, after pressure molding at a pressure of 300–1000 kg/cm$^2$, the material is baked for 1–3 hours at 1200°–1300° C.; the external shape is ground and an element is obtained.

However, the electrostrictive elements used in applications such as those aforementioned generally require a large amount of displacement. With the conventional electrostrictive elements the extent of the displacement is not sufficient and so it is necessary to apply an excessive voltage to the said electrostrictive elements to increase the amount of the displacement, but when such an excessive voltage is applied the insulation properties of the said element are reduced and, moreover, there is a further disadvantage in that shorting is liable to occur between a pair of adjacent electrodes.

The aim of this present invention is to eliminate such disadvantages of the conventional technology and provide novel solid state displacement elements with which the extent of displacement can be obtained by the application of a voltage.

SUMMARY OF THE INVENTION

As a result of thorough research carried out with a view to achieving the aforementioned aims in connection with this present invention, it was found that it was possible to make elements that were strained by the application of a voltage, by starting with the construction indicated below.

That is to say, in this present invention the elements have a completely novel structure in that they are solid state displacement elements wherein an intercalation compound comprised of an opposing inorganic layered compound and a polyar compound included between the said inorganic layered compound forms the principal component.

DESCRIPTION OF THE DRAWINGS

FIG. 4 is a diagrammatic representation of the relationship between the amount of strain and the intercalation rate of the polar compound.

Figure 1:
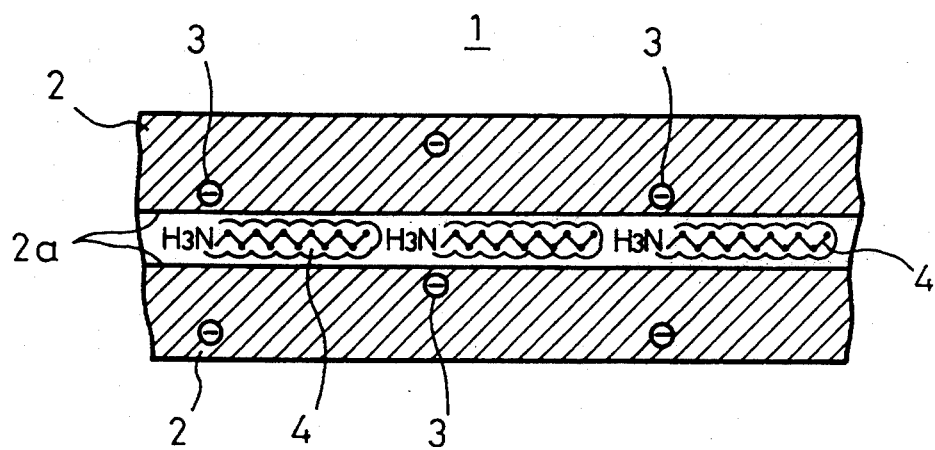
FIG. 1 is a schematic diagram showing a construction of this present invention.

The inventors have modeled the mechanism by which a strain is generated on the application of a voltage obtained with construction described above in the following way.

Thus, in this present invention, the intercalation compound when no voltage is being applied is in a state where the polar compound, which is intercalated between the inorganic layered compound, is completely or partially lying down, and the distance between the inorganic layered compound is satisfactorily small. However, when a voltage is applied across the inorganic layered compound, the polar compound is lined-up in the direction of the voltage and stands perpendicular to the inorganic layered compound or in steeply raised-up condition with respect thereto and the distance between the inorganic layered compound is extended and becomes longer than when no voltage is being applied.

By having intercalation compounds of this type as the principal component, it is possible to obtain solid state displacement elements that have a completely novel structure and with which a strain can be produced by the application of a voltage.

Thus, this present invention is one in which the change in distance between the inorganic layers due to the application of a voltage is first used for a solid state displacement element.

The intercalation of the polar compound with an intercalation rate of at least 20% with respect to the inorganic layered compound is desirable.

This is because an adequate extent of displacement cannot be obtained with the intercalation of the polar compound at an intercalation rate of less than 20%.

The inorganic layered compounds that can be used as raw materials in this present invention are inorganic compounds in which the crystal unit lattice has a crystal structure which is repeated in the thickness direction. Furthermore, the preferred compounds from among these inorganic layered compounds are the so-called inorganic layered compounds in which silicon oxide forms the principal component and which swells in water or other solvents and form fine scales (which is to say, a form wherein the particle diameter is large in comparison to the thickness). In practice, these compounds include mica based minerals such as muscovite mica and phlogovite mica, smectite based minerals such as vermiculite, montmorillonite and saponite, phyllosilicates of kaolin based minerals such as kaolinite, zirconium phosphate, layered polysilicates such as magadeite, layered titanates such as $V_2O_5$; $Na_2Ti_3O_7$, transition metal dicalcongenites such as $MoS_2$; and tungsten bronze based compounds such as $KNiAsO_4$; $HTaWO_6$.

On the other hand, the polar compounds that can be used in this present invention are compounds having at least one polar group. They also include compounds of which the polarity is further increased by ionization with acids for example. They may also be monomers that have polymerizable functional groups or polymers.

Here, the aforementioned polar groups defined in this present invention are groups in which there is at least one bond in the polar group that has a dipole moment of at least 0.7 Debye, and preferably at least 1.0 Debye. Actual examples of bonds of which the dipole moment is at least 0.7 Debye include N—H, O—H, H—F, H—Cl, C—F, C—Cl, C—Br, C—I, C—O, C=O and C=N, and examples of polar groups that have at least one of these bonds include hydroxyl group, amino group, carbonyl group, ether group, nitrile group, carboxyl group, amido group, imido group, pyrrolidone group etc., but the group is not limited to these groups in this present invention.

Moreover, the numerical value of the dipole moment adopted in this present invention is the value shown in "Kagaku Binran", Fundamentals II, p. 1406, table 11.173 (1975, Maruzen). That is to say, the Debye unit of dipole moment is $10^{-18}$ cgs.esu.cm.

Actual preferred examples of polar compounds that can be used in this present invention are indicated below.

(1) n-Hexylamine, (2) n-hexyl trimethyl ammonium bromide, (3) ethylene glycol, (4) glycine, (5) α-alanine, (6) α-aminovaleric acid, (7) iso-nicotinic, (8) urea, (9) p-nitroanilline, (10) p-aminobenzoic acid, (11) 3,5-diaminobenzoic acid, (12) 3,5-dinitrobenzoic acid, (13) formic acid, (14) acrylonitrile, (15) acetone, (16) acetamide (17) aniline and polymers thereof, (18) polyamino acids, and of these polar compounds those indicated in (1)-(9) are especially desirable.

Now, if the extent of the displacement of the layered compound is $\alpha$, in the case where the solid state displacement element is comprised of a materia in which n intercalation compound layers are laminated in parallel, formation, the total displacement of the element is theoretically $n \times \alpha$.

It has been possible by using solid state displacement elements according to this present invention to obtain an extent of displacement with an electric field with the application of a voltage by means of a completely novel structure.

DESCRIPTION OF THE PREFERRED EMBODIMENT

Figure 2:
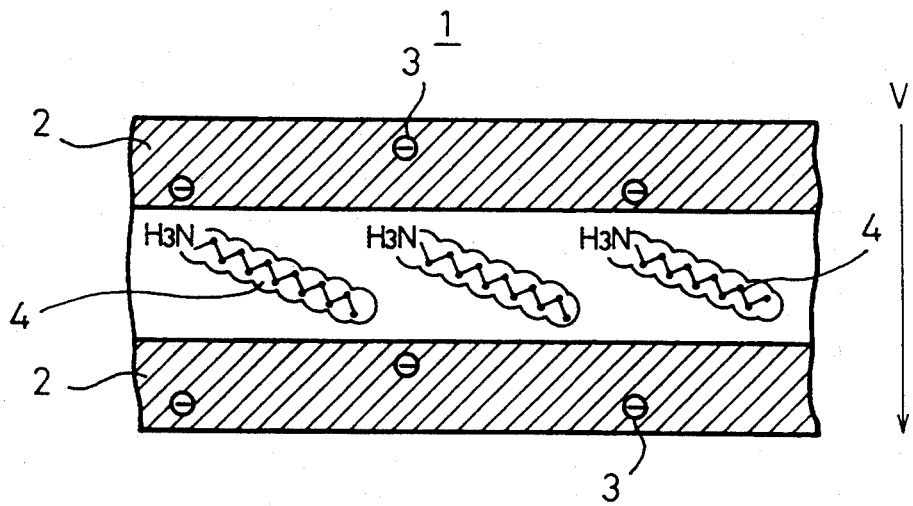
FIG. 2 is a schematic diagram showing the action of this present invention.

A part enlarged cross sectional drawing of an embodiment of a solid state displacement element is shown in FIG. 1, and a partly enlarged cross sectional drawing of the situation when a voltage has been applied to this embodiment of a solid state displacement element is shown in FIG. 2.

As shown in FIG. 1, the structure of the intercalation compound 1 of this embodiment has the polar compound 4 bonded to each of a plurality of negatively charged bonding sites 3 present on the layer surface 2a between the layers of the inorganic layered compound 2. Thus, in the state where no voltage has been applied, the polar compound 4 is limited by the steric structure of the intercalation compound 1 and it is completely, or to a certain extent, arranged lying along the layer surface 2a, and so the distance between the layers of the inorganic layered compound 2 is relatively small.

Next, when a voltage is applied in the direction perpendicular to the layer surface to this intercalation compound, as shown in FIG. 2, the polar compound 4 resists the limitation of the steric structure and is orientated along the direction in which the voltage is applied, and it adopts a state in which it is standing perpendicular to, or at an acute angle to, the layer surface 2a of the inorganic layered compound 2 and so the distance between the layers of the inorganic layered compound 2 becomes relatively large in comparison to that before the application of the voltage.

Furthermore, when the applied voltage is removed, the polar compound 4 reverts to its original state, assuming once again a state in which it is completely, or to a certain extent, lying along the surface layer 2a.

The extent to which the polar compound 4 is made to stand-up by the applied voltage corresponds to the height of the applied voltage.

Embodiment 1 is one in which the change in distance between the layers of the inorganic layered compound 2 is revealed as the extent of the displacement of a solid state displacement element on the basis of a mechanism, such as that outlined above, is taken as a first viewpoint and the extent of the displacement is large and, furthermore, it is one in which it is possible to obtain a solid state displacement where the extent of the displacement of the solid state displacement element can be controlled reversibly and continuously by controlling the application and removal of the voltage and the height of the applied voltage.

That is to say, a solid state displacement element according to embodiment 1 is constructed with a material comprised of an inorganic layered material 2 and a tray-like material comprised of the polar compound 4, and a strain is generated in the said material by the application of a voltage of a suitable value across the top and bottom flat surfaces.

The method of manufacturing a solid state displacement element in accordance with embodiment 1 is described below. First of all, a powder of the above mentioned inorganic layered compound 2 is dispersed in a suitable solvent to form a liquid suspension. Then, the above mentioned polar compound is taken in a liquid state and added gradually to the liquid suspension of the inorganic layered compound to form a mixed liquid suspension. As a result, the two are chemically bonded and a structure wherein the polar compound 4 is included between the inorganic layered compound, as shown in FIG. 1, can be obtained.

In order to make effective use of the individual electrostrictive characteristics of an intercalation compound 1 obtained in this way it is desirable that it should be formed in such a way that the intercalation compound 1 is arranged in parallel formation with lamination. In practice, flat plate-like solid state displacement elements are obtained by spreading the liquid suspension of the intercalation compound 1 on a flat plate and drying slowly a close to room temperature or by drying at room temperature −250°C. and then press molding.

Alternatively, with another method individual solid state displacement elements may be obtained by introducing the polar compound 1 that has been formed into a gaseous state into a powder of the inorganic layered compound 2, adding a binder such as poly(vinyl alcohol) and molding. Suitable electrodes are attached to the solid state displacement element in which the intercalation compound is the principal component that has been obtained in this way, and it is used as an electrostrictive element.

Actual embodiments are described below.

EMBODIMENT 1

Montmorillonite powder (a powder of an inorganic layered compound represented by the rational formula $Na_{0.33}Al_{2.37}Mg_{0.33}(Si_4O_{10})(OH)_2$, "Kunipia F", made by Kunimine Kogyo (Co.)) was immersed in a beaker which contained distilled water and a liquid suspension was obtained by stirring. An aqueous solution of n-hexylamine (Wako Junyaku Kogyo (Co.)), which is a polar compound ionized with hydrochloric acid was added while thoroughly stirring this liquid suspension and a homogeneous liquid suspension was obtained. The mixing ratio of the two materials was set at $2.5 \times 10^{-3}$ mol of n-hexylamine per gram of montmorillonite. The mixed liquid suspension was poured onto a teflon plate and spread so as to provide a uniform thickness and then dried at normal temperature. The material was then peeled from the teflon plate and was fabricated to obtain a flat plate-like element.

Figure 3:
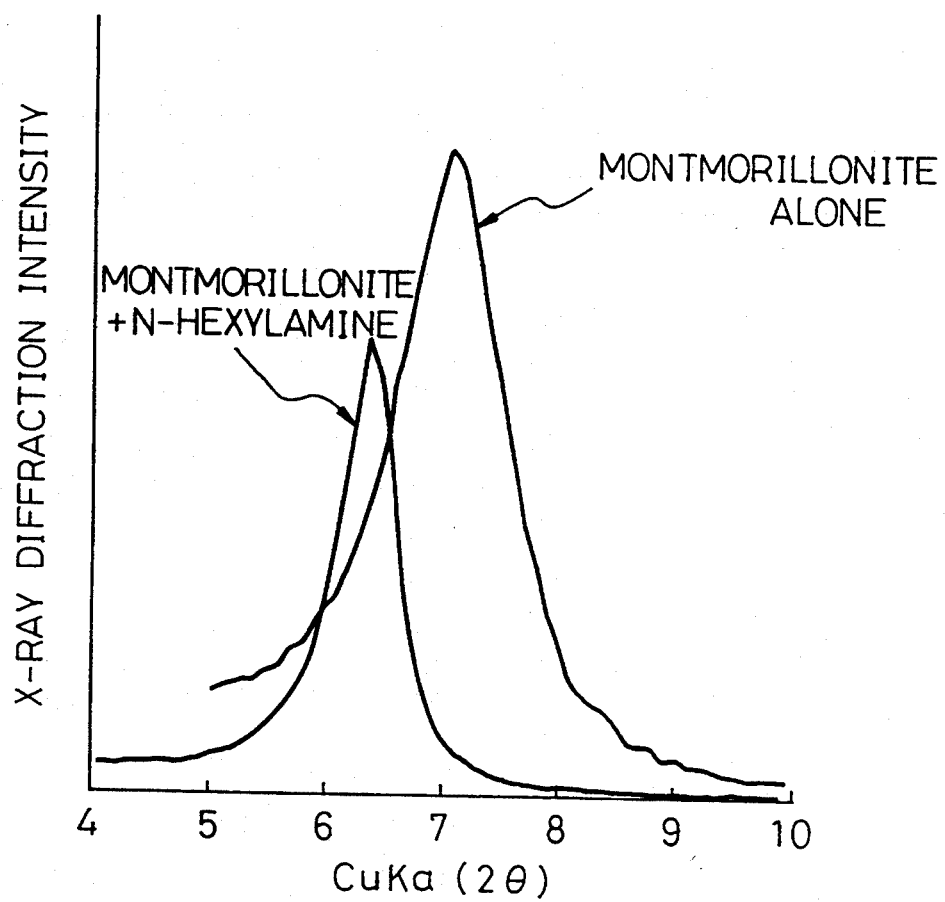
FIG. 3 is a diagram showing the results of the X-ray diffraction analysis of a solid state displacement element in accordance with this present invention.

Part of this element was pulverized and analyzed using the X-ray diffraction method and, as shown in FIG. 3, the results obtained indicated that the intercalation distance of the montmorillonite had a value larger than normal. This indicates that the n-hexylamine had been included between the layers of montmorillonite.

Furthermore, thermo-gravimetric analysis was carried out using the said powder. The results confirmed that the polar compound in the composition in embodiment 1 was intercalated and stable between the layers of montmorillonite up to a temperature of about 320° C. That is to say, since the organic compound forms an intercalation compound with the montmorillonite, which is an inorganic layered compound, it is possible to prevent dispersion of the polar compound even when it is heated to a temperature above its boiling point.

However, the polar compound that had been intercalated between the layers was dispersed from a temperature of about 320° C. and a pronounced loss in weight was observed. According to this loss in weight it was found that 25.0 wt. % of polar compound was intercalated between the montmorillonite layers. That is to say, the rate of intercalation of the polar compound that was contained between the inorganic layered compound in embodiment 1 was found to be 52.6%.

In the present invention, the intercalation rate means a ratio of an actual amount of the polar compound intercalated into the inorganic layered compound to the possible maximum amount of the same to be intercalated into the inorganic layered compound.

The displacement characteristics on applying a voltage of the solid state displacement element according to this present invention were investigated subsequently.

The intercalation compound that had been manufactured in the way described above was press molded into the form of a disc of 8 mm diameter and a thickness of 0.5 mm and, after the attachment of suitable electrodes, the extent of the displacement on applying a voltage of 500 V was measured.

The characteristics of the element indicated a large extent of displacement with a displacement of 0.5 $\mu$m, as shown in Table 1.

For comparison, the extent of the displacement on applying the same voltage to a disc shaped PZT element of 8 mm diameter and a thickness of 0.5 mm of the same shape is also indicated in Table 1.

The PZT was obtained using the same method of manufacturing as in the past, which is to say that 61.3 wt. % of PbO, 10.7 wt. % of $TiO_2$ and 21.1 wt. % of $ZrO_2$ were weighed out as the principal raw material and then mixed in a wet-type ball mill, after which the mixture was provisionally baked for 3–10 hours at 700°–900° C. and then mixed again in a ball mill and dried. Moreover, a binder such as poly(vinyl alcohol) was added and, after press molding at a pressure of 300–1000 kg/cm², the material was baked for 1–3 hours at 1200°–1300° C.; the external shape was ground and an element was obtained.

It is clear from Table 1 that the extent of the displacement on applying the same voltage to a conventional PZT element is 0.3 $\mu$m, while the extent of the displacement for the element of embodiment 1 was 0.5 $\mu$m and this element displayed a satisfactorily large value when compared with the conventional PZT element.

Moreover, the inventors have investigated the relationship between the extent of the strain and the intercalation rate of the polar compound contained between the layers of the montmorillonite. The results are shown in FIG. 4.

It is clear from FIG. 4 that shorting occurred on applying the voltage at 20% or less and measurements could not be made, and strain was first produced with an intercalation rate of 20%.

That is to say, if the intercalation rate is more than 20% it is possible to utilize the strain and, moreover, by setting the intercalation rate to 30% or above it is clearly possible to obtain a satisfactory extent of strain for a solid state displacement element.

EMBODIMENT 2

For embodiment 2, a synthetic saponite [rational formula $Na_{0.33}Mg_3(Si_{3.67}Al_{0.33})O_{10}(OH)_2$], which is an inorganic layered material powder, was immersed in distilled water and treated in the same way as in embodiment 1. n-Hexyl trimethyl ammonium bromide, which is a polar compound that had been dissolved in a suitable solvent, was added to this liquid suspension and a homogeneous liquid suspension was obtained by thorough stirring. The mixing ratio of the two materials was $2.5 \times 10^{-3}$ mol of n-hexyl trimethyl ammonium bromide per gram of synthetic saponite.

The mixed liquid suspension was poured over a teflon plate and spread so as to provide a uniform thickness and then dried at a normal temperature. The material was then peeled from the teflon plate and a flat plate-like element was obtained by working in the same way as in the case of embodiment 1.

Part of this element was powdered and subjected to X-ray diffraction analysis and thermo-gravimetric analysis and the results obtained were the same as those in the case of embodiment 1.

The displacement characteristics on applying a voltage of the solid state displacement element in accordance with embodiment 2 were investigated subsequently. The characteristics of the element (diameter 8 mm, thickness 0.5 mm) were as shown in Table 1.

As shown in Table 1, the solid state displacement element of embodiment 2 also had a large amount of displacement at 0.5 $\mu$m, and it exhibited a satisfactorily large value when compared with the extent of displacement of 0.3 $\mu$m of a conventional PZT element (diameter 8 mm, thickness 0.5 mm).

In the present invention, it is thought that the actual element described above acted in such a way that the polar compound that had been included between the layers of the inorganic layered compound were orientated along the direction in which the voltage was being applied by the electric field due to the applied voltage of 500 V, and that the distance between the layers increased thereby and this provided the large extent of displacement of 0.5 $\mu$m as shown in Table 1.

EMBODIMENT 3–EMBODIMENT 9

In embodiments 3–9, the compounds shown in Table 1 as polar compounds were added while stirring the compounds shown in Table 1 as inorganic layered compounds. Here, the mixing ratio of the two materials was set at $2.5 \times 10^{-3}$ mol of polar compound per gram of the inorganic layered compound. The liquid suspension obtained in this way in each case was treated using the same procedure as in embodiment 1 and flat plate-like elements were obtained.

The extent of strain of each element obtained was measured under the same conditions as in embodiment 1 and the results obtained are shown in Table 1.

As shown in table 1, the element obtained in embodiment 3 could be made to produce a strain by the application of a voltage.

[TABLE 1]

| | Inorganic Layered Compound | Polar Compound | Extent of Displacement |
|---|---|---|---|
| Embodiment 1 | Montmorillonite | n-Hexylamine | 0.5 μm |
| Embodiment 2 | Synthetic Saponite | n-Hexyl trimethyl ammonium bromide | 0.5 μm |
| Embodiment 3 | Montmorillonite | Ethylene glycol | 0.3 μm |
| Embodiment 4 | ↑ | Glycine | 0.4 μm |
| Embodiment 5 | Synthetic Saponite | α-Alanine | 0.2 μm |
| Embodiment 6 | ↑ | α-Amino-valeric acid | 0.2 μm |
| Embodiment 7 | ↑ | Isonicotinic acid | 0.2 μm |
| Embodiment 8 | Zirconium phosphate | Urea | 0.4 μm |
| Embodiment 9 | ↑ | p-Nitroaniline | 0.3 μm |
| Comparative Example | PZT Element | | 0.3 μm |

We claim:

1. A solid state displacement element comprising: an intercalation compound comprising inorganic layered compounds opposing each other, and a polar compound placed between said inorganic layered compounds, so that a distance formed between said inorganic compounds is extended when a voltage is applied across said intercalation compound, wherein said solid state displacement element is molded by a press-molding operation; and said polar compound is at least one compound selected from the group consisting of n-hexylamine and n-hexyl trimethyl ammonium bromide.

2. A solid state displacement element according to claim 1 wherein at least 20% of said polar compound is intercalated into said inorganic layered compounds with respect to a possible amount of said polar compound to be intercalated into said inorganic layered compounds.

3. A solid state displacement element according to claim 1 wherein said inorganic layered compound is at least one compound selected from the group consisting of a mica based mineral, a smectite based mineral, a phyllosilicate of a kaolin based mineral, a layered polysilicate, a transition metal dicalcogenite, and a tungsten bronze based compound.

4. The solid state displacement element according to claim 3, wherein said mica based mineral is selected from the group consisting of muscovite mica and phlogopite mica; said smectic base mineral is selected from the group consisting of vermiculite, montmorillomite, and saponite; and phyllosilicate of a kaolin based mineral is selected from the group consisting of kaolinite and zirconium phosphates; said layered polysilicate is selected from the group consisting of magadeite, and a layered titanate; said transitional metal dicalcogenite is $MoS_2$; and said tungsten bronze based compound is selected from the group consisting of $KNiAsO_4$ and $HTaWO_6$.

5. The solid state displacement element according to claim 4, wherein said layered titanate is selected from the group consisting of $V_2O_5$ and $Na_2Ti_3O_7$.

6. A solid state displacement element comprising: an inter-layer compound comprised of a layered inorganic compound and a polar compound as the principal component, such that application of a voltage across said element expands the distance between said layers; said polar compound being at least one compound selected from the group consisting of n-hexylamine and n-hexyl trimethyl ammonium bromide.

7. A solid state displacement element according to claim 6 wherein said inter-layer compound contains at least 20% of said polar compound.

8. A solid state displacement element comprising an intercalation compound as defined in any one of claims 1–3 or 6–7 such that said compound expands said element upon application of a voltage across element.

9. A solid state displacement element comprising an intercalation compound as a main element, said intercalation compound comprising inorganic layered compounds, each being oppositely arranged; and a polar compound interposed in a space formed between said inorganic layered compounds arranged oppositely to each other, said element being strained when electrical voltage is applied thereto; said polar compound being at least one compound selected from the group consisting of n-hexylamine and n-hexyl trimethyl ammonium bromide.

10. A solid state displacement element comprising: an intercalation compound comprising inorganic layered compounds opposing each other, and a polar compound placed between said inorganic layered compounds so that a distance formed between said inorganic compounds is extended when a voltage is applied across said intercalation compound, wherein said inorganic layered compound is selected from inorganic layered compound group which swell in water or other solvents and said polar compound is selected from polar compound group having a dipole moment of at least 0.7 Debye; said polar compound being at least one compound selected from the group consisting of n-hexylamine and n-hexyl trimethyl ammonium bromide.

11. A solid state displacement element according to claim 10, wherein said solid state displacement element is molded by press-molding operation.

12. A solid state displacement element according to claim 10, wherein said polar compound is selected from polar compound group having a dipole moment of more than 1.0.

13. A solid state displacement element according to claim 10, wherein said inorganic layered compound is selected from mica base minerals having at least one of negative electric charge and positive electric charge on a surface of said layered compound.

* * * * *